United States Patent [19]

Wang et al.

[11] Patent Number: 6,011,196
[45] Date of Patent: Jan. 4, 2000

[54] ABSORBENT MATERIAL HAVING IMPROVED ABSORBENT PERMEABILITY AND METHODS FOR MAKING THE SAME

[75] Inventors: Lin Wang; Ebrahim Rezai; Yumiko Hayashi, all of Kobe; Eui-Boo Cho, Hyogo, all of Japan

[73] Assignee: The Procter & Gamble Company, Cincinnati, Ohio

[21] Appl. No.: 09/051,682

[22] PCT Filed: Oct. 1, 1996

[86] PCT No.: PCT/US96/15645

§ 371 Date: Apr. 16, 1998

§ 102(e) Date: Apr. 16, 1998

[87] PCT Pub. No.: WO97/12575

PCT Pub. Date: Apr. 10, 1997

[30] Foreign Application Priority Data

Oct. 3, 1995 [AU] Australia ................. PN 5371

[51] Int. Cl.[7] ............... A61F 13/15; B01J 20/22; B32B 5/16

[52] U.S. Cl. ............ 604/368; 502/401; 428/402
[58] Field of Search ............ 604/368; 502/401; 428/402

[56] References Cited

U.S. PATENT DOCUMENTS 5,851,672  12/1998  Wang et al. ............... 428/407

*Primary Examiner*—John G. Weiss
*Assistant Examiner*—Catherine Cogut
*Attorney, Agent, or Firm*—Edward J. Milbrada; Steven W. Miller; Jacobus C. Rasser

[57] ABSTRACT

An absorbent material with substantially improved liquid permeability such that it is not subject to gel blocking while maintaining a preferred absorbent capacity is disclosed. The absorbent material is in particulate form and is the reaction product of a water-insoluble, absorbent, hydrogel-forming polymer and a polycationic polymer, the reaction forming a covalent bond between the polymers. After the reaction, the absorbent material has a Saline Flow Conductivity greater than $(500-11.5 \cdot GV)(10^{-7})$ cm$^3$ sec/g where GV is the gel volume of the absorbent material.

21 Claims, 4 Drawing Sheets

ABSORBENT MATERIAL HAVING IMPROVED ABSORBENT PERMEABILITY AND METHODS FOR MAKING THE SAME

FIELD

The present invention relates to an absorbent material which, upon contacting liquids such as water, body exudates and the like, swells and imbibes such liquids; a method of making such absorbent materials; and absorbent articles such as diapers, adult incontinence pads, sanitary napkins, and the like, incorporating such absorbent materials.

BACKGROUND

Water-insoluble, water-swellable, hydrogel-forming absorbent polymers are capable of absorbing large quantities of liquids such as water, body exudates or fluids (e.g., urine, blood, menstrual fluid), industrial fluids and household; fluids and are further capable of retaining such absorbed liquids under moderate pressures. The absorption characteristics of such polymer materials make them especially useful for incorporation into absorbent articles such as disposable diapers, adult incontinence pads and briefs, catamenial products such as sanitary napkins, and the like.

The development of highly absorbent members used in such absorbent articles are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids; in particular, urine. In this regard, the use of certain absorbent polymers often referred to as "hydrogels," "superabsorbents" or "hydrocolloid" material has been particularly important. See, for example, U.S. Pat. No. 3,699,103 (Harper et. al), issued Jun. 13, 1972, and U.S. Pat. No. 3,770,731 (Harmon), issued Jun. 20, 1972, which disclose the use of such absorbent polymers (hereafter "water-insoluble, absorbent, hydrogel-forming polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et. al), issued Jun. 16, 1987 and U.S. Pat. No. 4,935,022 (Lash et. al), issued Jun. 19, 1990, which disclose dual-layer core structures comprising a fibrous matrix and hydrogel-forming absorbent polymers useful in fashioning thin, compact, non-bulky diapers.

Prior absorbent structures have generally comprised relatively low amounts (e.g., less than about 50% by weight) of water-insoluble, absorbent, hydrogel-forming polymers. There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking when they are used in absorbent articles in a high concentration. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent member are fully saturated or before the fluid can diffuse or wick past the "blocking" particles into the rest of the absorbent member. Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et. al), issued May 30, 1989.

This gel blocking phenomena has typically necessitated the use of a fibrous matrix in which the particles of hydrogel-forming absorbent polymer are dispersed. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735 (Alemany et. al), issued May 30, 1989. However, dispersing the hydrogel-forming absorbent polymer in a fibrous matrix at relatively low concentrations in order to minimize or avoid gel blocking may lower the overall fluid storage capacity of thinner absorbent structures. Using lower concentrations of these hydrogel-forming absorbent polymers limits somewhat the real advantage of these materials, namely their ability to absorb and retain large quantities of body fluids per given volume.

In general, increasing the gel strength of hydrogel-forming absorbent polymers can contribute to decreased gel blocking. Gel strength relates to the tendency of the hydrogel formed from these polymers to deform or "flow" under usage stresses. Gel strength needs to be such that the hydrogel formed does not deform and fill to an unacceptable degree the capillary void spaces in the absorbent structure or article, thereby inhibiting the absorbent capacity of the structure/article, as well as the fluid distribution through the structure/article. High gel strength is usually obtained by crosslinking. It is believed that crosslinking increases the resistance to deformation of hydrogel-forming absorbent polymer surfaces. However, normal crosslinking has a deep impact on the absorbent capacity of a hydrogel-forming absorbent polymer. In general, absorbent capacity or "gel volume" has inverse power-law dependence on the level of crosslinking. That is, high crosslinking level results in high gel strength but low gel volume. Gel volume be a measure of the amount of water or body fluids that a given amount of hydrogel-forming polymer can absorb. It is required that gel volume is sufficiently high in order that the hydrogel-forming polymer can absorb significant amounts of the aqueous body fluids encountered during use of the absorbent article.

Another important factor that has to be considered is the liquid permeability of hydrogel-forming absorbent polymers. It has been discovered that the permeability or flow conductivity of the gel layer formed by swelling in the presence of body fluids is extremely important when these absorbent polymers are used in absorbent cores or members at a high concentration in localized or throughout regions thereof. It should be noted that lack of liquid permeability or flow conductivity of absorbent polymers may directly impact on the ability of resultant gel layers to acquire and distribute body fluids.

Based on the foregoing, there is a need for an absorbent material which has improved fluid absorbency and fluid permeability.

SUMMARY

The present invention is directed to an absorbent material having improved fluid absorbency and fluid permeability.

In one aspect of the present invention, the absorbent material comprises (a) a plurality of absorbent gelling particles comprising a water-insoluble, absorbent, hydrogel-forming polymer and (b) a polycationic polymer covalently bonded to the absorbent gelling particles; wherein the absorbent material has a Saline Flow Conductivity, greater than $(500-11.5 \cdot GV) \cdot (10^{-7})$ cm$^3$ sec/g, wherein GV is the gel volume of the absorbent material.

In another aspect of the present invention, the absorbent article comprises (a) a liquid pervious topsheet, (b) a liquid impervious backsheet, and (c) an absorbent core positioned between the topsheet and the backsheet, wherein the absorbent core comprises the above described absorbent material.

The present invention also relates to a method for making an absorbent material comprising (a) preparing a solution containing a polycationic polymer and a solvent; (b) applying the solution onto a plurality of absorbent gelling particles comprising a water-insoluble, absorbent, hydrogel-forming polymer; and (c) reacting the polycationic polymer with the absorbent gelling particles such that the resulting the absorbent material has a Saline Flow Conductivity greater than $(500-11.5 \cdot GV) \cdot (10^{-7})$ cm$^3$ sec/g., wherein GV is the gel volume of the absorbent material.

The present invention further relates to a method for making an absorbent material comprising (a) preparing a solution containing a polycationic polymer and a solvent; (b) applying the solution onto a plurality of absorbent gelling particles comprising a water-insoluble, absorbent, hydrogel-forming polymer; (c) reacting the polycationic polymer with the absorbent gelling particles; (d) removing the solvent from the resulting material; and (e) heating the resulting material of step (d) at a temperature of from about 100° C. to about 350° C. sufficient to achieve at least 80% by weight of the polycationic polymer covalently bonded to the absorbent gelling particles.

These and other features, aspects, and advantages of the present invention will become better understood with regard to the following description, appended claims and accompanying drawing.

DETAILED DESCRIPTION

The following is a list of definitions for certain terms used herein:

"Comprising" means other steps and other ingredients which do not affect the end result can be added. The term encompasses the terms "consisting of" and "consisting essentially of".

"GV" means gel volume.

"SFC" means Saline Flow Conductivity.

"WAHP" means water-insoluble, absorbent, hydrogel-forming polymer.

A. Absorbent Material

The absorbent material of the present invention is capable of absorbing large quantities of liquids such as water, body fluids, industrial fluids and household fluids at a rapid rate. In particular, the absorbent material of the present invention has a high degree of permeability while also having a high degree of absorbent capacity, and structural integrity or strength. It is the combination of high permeability and high absorbent capacity which forms the basis for the instant invention over past absorbent materials which have not provided such a combination to the extent now achieved.

The absorbent material of the present invention comprises: (a) a plurality of absorbent gelling particles comprising a WAHP; (b) a polycationic polymer covalently bonded to the absorbent gelling particles, wherein the absorbent material has a Saline Flow Conductivity, greater than $(500-11.5 \cdot GV) \cdot (10^{-7})$ cm$^3$ sec/g, wherein GV is the gel volume of the absorbent material.

The polycationic polymer used herein is a polymer which has multiple functional groups that are capable of covalently bonding to the surface of the absorbent gelling particles.

Covalently bonded refers to chemical bonding involving the sharing of electron pairs between two chemical substances, i.e. between the polycationic polymer and the WAHP of the absorbent gelling particles. Preferably, at least about 80%, more preferably at least about 90%, by weight of the polycationic polymer in the absorbent material is covalently bonded to the WAHP of the absorbent gelling particles. The amount of polycationic polymers that are bonded to the absorbent material is evaluated by measuring the Percentage of Covalently Bonded Polycationic Polymer (PCBPP). "Percentage of Covalently Bonded Polycationic Polymer (PCBPP)" is defined as the percentage of polycationic polymer that is not extractable by extracting the absorbent material with an acidic solution. Methods for determining the PCBPP of the absorbent material are provided hereafter in the Test Method Section.

While not intending to be bound by theory, it is believed that the superior liquid permeability achieved by the absorbent material of the invention occurs as a result of the chemical reaction between the polycationic polymer and the WAHP on the surface of the absorbent gelling particles. In preferred embodiments, the WAHP of the absorbent gelling particles preferably includes a carboxy (e.g. —COOH) functional group, especially at the surface of the particles, which is reactive with an amino (e.g. NH$_2$) functional group typically included in the polycationic polymer. Thus, a covalently bond between the WAHP and polycationic polymer (—COOH+—NH$_2$→—CONH—) is made mainly at the surface of the absorbent gelling particles so as to form relatively rigid or hard particles. Such rigid or hard particles consequently have the ability to maintain their relative shape even when subjected to large amounts ("gushes") of fluids under pressure. Preferably such reaction mainly occurs at the surface, thereby forming a surface crosslinked shell via a polymer crosslinker. Consequently, the absorbent capacity can be maintained or only minimally affected. In other words, as the absorbent gelling particles will not be subjected to gross deformation upon swelling with fluid, any remaining fluid will be able to permeate through the interstitial voids between the particles at a rapid rate, to seek any remaining absorbent gelling particles which are not completely satiated.

In a preferred embodiment, an amino-group or imine-group containing polymer is used as the polycationic polymer. Such polycationic polymers include polyamines, polyimines and mixtures thereof. More preferably, the polyamine is selected from the group consisting of polymers having primary amine groups (e.g., polyvinylamine, polyallylamine) and polymers having secondary amine groups (e.g., polyethyleneimines). The polyimines preferably used include polyethyleneimines, modified polyethyleneimines crosslinked with epihalohydrine, and mixtures thereof. Other suitable polycationic polymers include modified polyamidoamine grafted with ethyleneimine, polyetheramine, polyvinylamine, polyallylamine, polyamidopolyamine and mixtures thereof.

In a preferred embodiment, the polycationic polymer is a cationic polymer having an average molecular weight of at least about 200, more preferably of at least more than 5,000, and most preferably of more than about 10,000. The polycationic polymers useful in the invention include those polymers having a single maximum value (a peak) in molecular weight distribution, as well as those polycationic polymers having one or more maximum values. The molecular weight distribution can be analyzed by, for example, gel permeation chromatography.

Preferably, the amount of polycationic polymer used in the absorbent material is from about 0.05 to 10% by weight of the absorbent gelling particles, more preferably from about 0.1 to about 5% and most preferably from about 0.3 to about 3% by weight of the gelling particles.

The liquid permeability of the absorbent material of the present invention is measured and defined by the SFC Test. The SFC is a physical property of the absorbent material which indicates the liquid permeability or flow conductivity when the absorbent material is exposed to saline containing fluids and after swells, which are typically associated with the human body. The SFC provides a measure of the ability of a swollen absorbent material to transport saline fluids through its structure.

The absorbent capacity of the absorbent material of the present invention is measured and defined by the GV Test. The GV of an absorbent material is a physical property of the absorbent material which indicates the absorbent capacity when the absorbent material is exposed to saline containing fluids and after swells. It provides a measure of the maximum absorbent capacity of the material under the condition of use. In a preferred embodiment, the GV of the absorbent material is at least about 30 g/g, and more preferably at least about 40 g/g. Methods for measuring the SFC and GV of absorbent materials are described hereafter in the Test Method Section.

Figure 1:
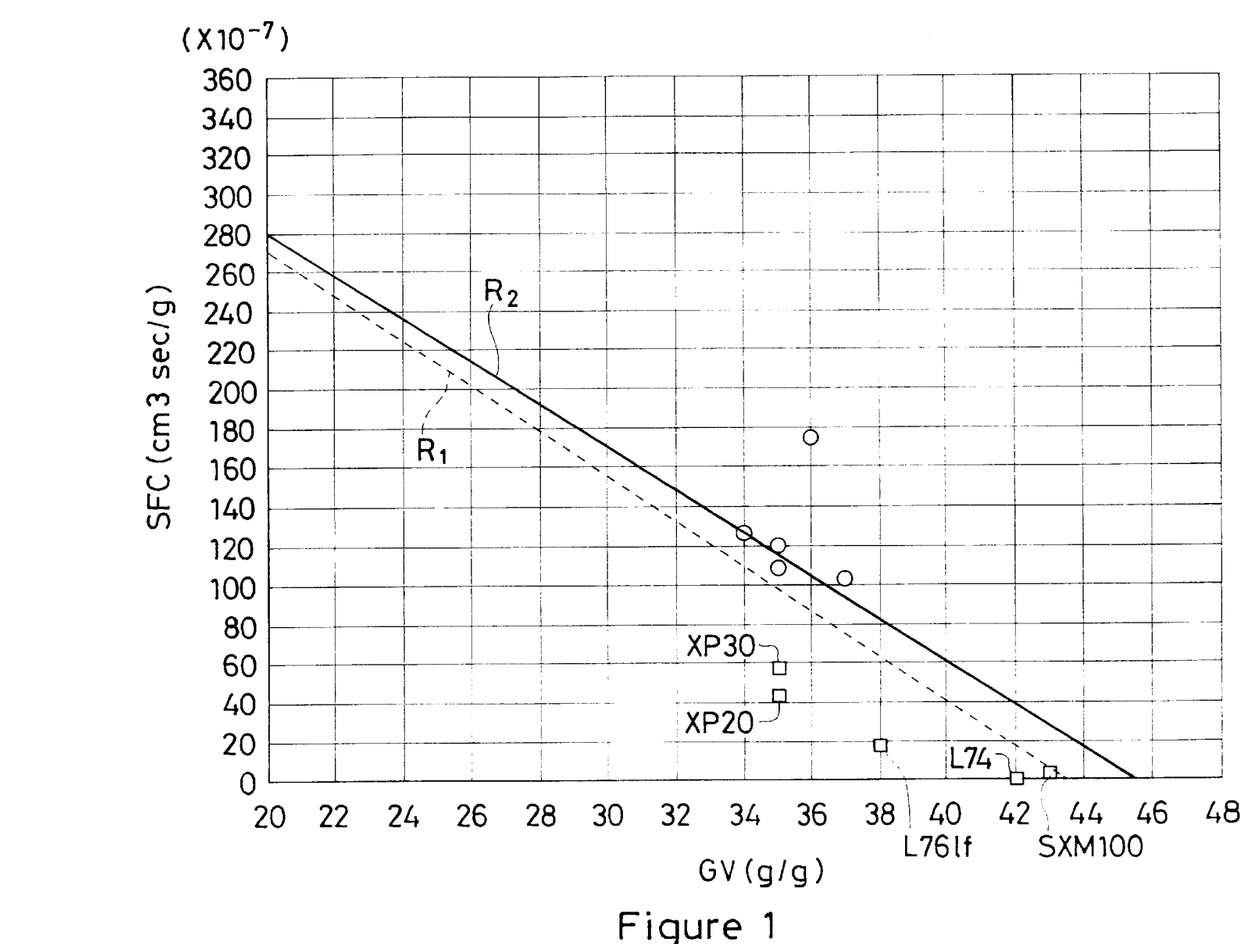
FIG. 1 is a diagram showing the relationship between gel volume ("GV") and the Saline Flow Conductivity ("SFC").

Referring to FIG. 1, the line R1 shows the relation $SFC=(500-11.5 \cdot GV)-(10^{-7})$ cm$^3$ sec/g, wherein the horizontal axis indicates the GV value (g/g), while the vertical axis indicates the SFC value (cm$^3$sec/g). Therefore, the absorbent material of the invention has the SFC value and GV value in the upper area of the line R1.

In a preferred embodiment, the absorbent material has a SFC of at least about $20 \cdot (10^{-7})$ cm$^3$ sec/g.

In a more preferred embodiment, the absorbent material has a SFC greater than $(500-11.0 \cdot GV) \cdot (10^{-7})$ cm$^3$ sec/g. Therefore, such absorbent material has the SFC value and GV value in the upper area of the line R2 which shows the relation $SFC=(500-11.0 \cdot GV) \cdot (10^{-7})$ cm$^3$ sec/g.

B. Water-insoluble, Absorbent, Hydrogel-forming Polymer

1. Chemical Composition

The WAHPs useful in the present invention are commonly referred to as "hydrogel-forming", "hydrocolloids", or "superabsorbent" polymers and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, WAHPs useful in the present invention have a plurality of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, preferably in minor amounts, in preparing the WAHPs herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et. al), issued Feb. 28, 1978, and in U.S. Pat. No. 4,062,817 (Westerman), issued Dec. 13, 1977.

Olefinically unsaturated carboxylic acid and carboxylic acid anhydride monomers include the acrylic acids typified by acrylic acid itself, methacrylic acid, ethacrylic acid, -chloroacrylic acid, a-cyanoacrylic acid, -methylacrylic acid (crotonic acid), -phenylacrylic acid, -acryloxypropionic acid, sorbic acid, -chlorosorbic acid, angelic acid, cinnamic acid, p-chlorocinnamic acid, -sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred WAHPs for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 4,076,663 (Masuda et. al), issued Feb. 28, 1978, U.S. Pat. No. 4,093,776 (Aoki et. al), issued Jun. 6, 1978, U.S. Pat. No. 4,666,983 (Tsubakimoto et. al), issued May 19, 1987, and U.S. Pat. No. 4,734,478 (Tsubakimoto et. al), issued Mar. 29, 1988.

More preferably polymer materials used in making the hydrogel-forming polymers are slightly network crosslinked polymers of partially neutralized polyacrylic acids and starch derivatives thereof. More preferably still, the hydrogel-forming polymers comprise from about 50 to about 95%, more preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the WAHPs. Processes for network crosslin king these polymers and typical network crosslinking agents are described in greater detail in U.S. Pat. No. 4,076,663 (Masuda et. al), issued February 28.

Surface crosslinked hydrogel-forming polymers are preferably used in a preferred embodiment of the present invention. They have a higher level of crosslinking in the vicinity of the surface than in the interior. As used herein, "surface" describes the outer-facing boundaries of, e.g., the particle, fiber. For porous hydrogel-forming absorbent polymers (e.g., porous particles), exposed internal boundaries can also be included. By a higher level of crosslinking at the surface, it is meant that the level of functional crosslinks for the WAHP in the vicinity of the surface is generally higher than the level of functional cross links for the WAHP in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given WAHP. For particulate hydrogel-forming polymers, surface crosslinking can vary with particle size, porosity, etc. Depending on variations in surface/volume ratio within the WAHP (e.g., between small and large particles), it is not unusual for the overall level of crosslinking to vary within the material (e.g., be greater for smaller particles).

Surface crosslinking is generally accomplished after the final boundaries of the WAHP are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

The surface crosslinking can be accomplished before or, simultaneously, with the covalent bonding of the polycationic polymer to the surface of the absorbent gelling particles.

While the WAHP is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

2. Physical Forms

The absorbent gelling particles used in the present invention can have a size, shape and/or morphology varying over a wide range. The absorbent gelling particles may have a large ratio of greatest dimension to smallest dimension (e.g., granules, flakes, pulverulents, interparticle aggregates, interparticle crosslinked aggregates, and the like) and can be in the form of fibers, foams, and the like.

For particles of WAHPs useful in the present invention, the median particle size is in the range of from about 100 to about 800 microns, preferably in the range of from about 200 to about 600 microns, and more preferably in the range of from about 250 to about 500 microns. The WAHPs can also comprise mixtures with low levels of one or more additives, such as for example powdered silica, surfactants, glue, binders, and the like. The components in this mixture can be physically and/or chemically associated in a form such that the WAHP component and the non-hydrogel-forming polymer additive are not readily physically separable. The WAHPs can be essentially non-porous or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S. Series Alternate Sieve Designation) is considered to have a particle size between 500 and 710 microns; and a particle that passes through a sieve with 500 micron openings is considered to have a size less than 500 microns. The mass median particle size of a given sample of WAHP particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the WAHP particles are further described in U.S. Pat. No. 5,061,259 (Goldman et. al), issued Oct. 29, 1991.

C. Process for Making Absorbent Material

The present invention also provides a method for making the absorbent material. The method comprises (a) preparing a solution containing a polycationic polymer and a solvent; (b) applying the solution to a plurality of absorbent gelling particles comprising WAHP; and (c) reacting the polycationic polymer with the absorbent gelling particles such that the resultant absorbent material has a SFC greater than $(500-11.5 \cdot GV) \cdot (10^{-7})$ cm$^3$ sec/g, wherein GV is the gel volume of the absorbent material.

In a preferred embodiment, the solution is prepared by mixing the polycationic polymer with the solvent such mixing can be accomplished by a variety of ways well known in the art, including, for example, mechanical stirring and/or shaking.

In a preferred embodiment, a polar solvent, more preferably a polar organic solvent, is used as the solvent in step (a). The polycationic polymer, preferably comprises from about 0.05% to about 60%, more preferably from about 0.5% to about 30% by weight of the solution. In a more preferred embodiment, water and optionally an polar organic solvent make up the balance of the solution. Preferably, the organic solvent and water are contained in a weight ratio from about 2:98 to about 98:2. In a more preferred embodiment, the weight ratio of the polycationic polymer to the absorbent gelling particles is from about 0.05:100 to about 10:100, more preferably from about 0.1:100 to about 3:100.

Preferred polar organic solvents useful in the present invention include, but are not limited to, methanol, ethanol, or propanol; acetone; dimethylformamide (DMF); dimethylsulfoxide (DMSO); hexylmethyl-phosphoric triamide (HMPT); and mixtures thereof. Alternatively, a mixture of a polar organic solvent and a non-polar solvent can be used. Such non-polar organic solvents are well known and include hexane, toluene, xylene, and benzene.

In a preferred embodiment, the polycationic polymer comprises from about 0.05% to about 60%, more preferably from about 0.5% to about 30% by weight of the solution. In a more preferred embodiment, the weight ratio of the polycationic polymer to the absorbent gelling particles is from about 0.05:100 to about 10:100, more preferably from about 0.1:100 to about 3:100.

The solution containing the polycationic polymer is then applied to a plurality of the absorbent gelling particles. In particular, at least two, preferably all, of the absorbent gelling particles have at least some portion covered with the solution. In a preferred embodiment, at least 70% of the surface area of the gelling particles is covered with the solution applied thereon. The solution can be applied using any of the various techniques and apparatus well known in the art which are suitable for applying a solution to a material including coating, dumping, pouring, dropping, spraying, atomizing, condensing, or immersing the solution onto the absorbent gelling particles.

In a preferred embodiment, the polycationic polymer is mixed with the absorbent gelling particles so that more than about 90% of the surface area of the gelling particles is covered with the solution. The mixing can be accomplished by using various ways known in the art, including mechanical stirring, shaking.

In a preferred embodiment, the polycationic polymer are reacted with the absorbent gelling particles such that the polycationic polymer becomes covalently bonded to the absorbent gelling particles at the surface area of the absorbent gelling particles. More preferably, the covalent bonds are made between the surface-located carboxy groups of the absorbent gelling particles and the amino groups of the polycationic polymer. Optionally, catalysts, such as a Lewis-base or Lewis-acid catalyst, plasma irradiation, or photo-irradiation, can be used to help the formation of covalent bonds between the polycationic polymer and the gelling particles.

In a preferred embodiment, at least about 80% more preferably more than about 90% by weight of the polycationic polymer is covalently bonded to the absorbent gelling particles.

In a more preferred embodiment, reaction step (c) further comprises heating the resulting material of step (b). More specifically, the absorbent gelling particles and the applied solution are heated thereby facilitating the reaction between the polycationic polymer and the WAHP.

In a more preferred embodiment, reaction step (c) further comprises removing the solvent from the resulting material before the heating step. Such solvent removal can include, but not be limited to, evaporation.

Preferably heating of the material resulting from step (b) is carried out at a temperature of from about 100° C. to about 350° C., more preferably from about 150° C. to about 250° C., such that at least about 80% by weight of the polycationic polymer is covalently bonded to the absorbent gelling particles. The required time for heating depends upon a variety of factors, including the temperature of heating source, the presence and/or type and/or amount of catalyst (s), the polycationic polymer(s) and the total amount of material to be heated. Preferably an absorbent material according to the invention can be obtained by heating for a time period preferably of from about 10 minutes to about 2 weeks, more preferably from about 30 minutes to about 600 minutes for temperatures from about 100° C. to about 350° C. For example, when the heating is conducted at 200° C. without any catalyst, the time period of from about 30 minutes to about 150 minutes is preferred. In another example, when the heating is conducted 150° C. without any catalyst, the time period of about 360 minutes is preferred.

D. Absorbent Article Comprising the Absorbent Materials

The absorbent materials according to the present invention can be used for many purposes in many fields of use. For example, the absorbent material can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials. In these environments, the absorbent material of the invention can have a number of shapes and sizes. For example, the absorbent material can be in the form of particles, sheets, films, cylinders, blocks, fibers, filaments, or other shaped elements. The absorbent material can comprise a cellulosic material for enhancing absorbency and/or be in a form amenable to these and other applications as described hereinafter.

Because of the unique absorbent properties of the absorbent material of the present invention, it is especially suitable for use as an absorbent core in absorbent articles, especially disposable absorbent articles. As used herein, the term "absorbent article" refers to articles which absorb and contain body fluids and more specifically refers to articles which are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted).

In general, an absorbent article comprise (a) a liquid pervious topsheet, (b) a liquid impervious backsheet, and (c) an absorbent core positioned between the topsheet and the backsheet. As used herein, the term "absorbent core" refers to the component of the absorbent article that is primarily responsible for fluid handling properties of the article, including acquiring, transporting, distributing and storing body fluids. As such, the absorbent core preferably does not include the topsheet or backsheet of the absorbent article.

The absorbent core used in the present invention an absorbent material of the present invention. The absorbent core further comprises two layered tissues wherein the absorbent material is distributed between the two layered tissues.

In a more preferred embodiment, the absorbent material in the absorbent core has a basis weight of from about 40 g/m$^2$ to about 1500 g/m$^2$, more preferably from about 100 g/m$^2$ to about 1000 g/m$^2$, more preferably still from about 150 g /m$^2$ to about 500 g/m$^2$ of the absorbent material.

In one certain embodiment, the absorbent core or absorbent member can further comprise fibers or fluff pulp (fibrous or fiber material); more specifically, non-absorbent-gelling fibers. Such fiber material can be used as a reinforcing or absorbent member in the absorbent core, improving fluid handling of the core, as well as serving as a co-absorbent with the absorbent polymers. As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

Preferably, the absorbent core or absorbent member includes from about 40% to about 100% by weight of the absorbent material and from about 60% to about 0% by weight of such non-absorbent-gelling fiber material distributed within the absorbent material.

In a preferred embodiment, the absorbent material is in a concentration of at least about 40%, more preferably from about 45 to about 100% by weight in at least one region of the absorbent core. In a more preferred embodiment, the absorbent member comprises a fibrous matrix wherein the absorbent material is distributed in the fibrous matrix.

Any type of fiber material which is suitable for use in conventional absorbent products can be used in the absorbent core or absorbent member herein. Specific examples of such fiber material include cellulose fibers, improved cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the absorbent core by virtue of their good wicking properties. This is because, in the absorbent core herein, the wicking propensity of the fibers is as important, if not more important, than the absorbent capacity of the fiber material itself due to the high rate of fluid uptake and lack of gel blocking properties of the absorbent core. Synthetic fibers are generally preferred for use herein as the fiber component of the absorbent core. More preferred are polyolefin fibers, preferably polyethylene fibers.

Other cellulosic fiber materials which can be useful in certain absorbent cores or absorbent members herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et. al), issued Dec. 19, 1989; U.S. Pat. No. 4,889,595 (Herron et. al), issued Dec. 26, 1989; U.S. Pat. No. 4,889,596 (Schoggen et. al), issued Dec. 26, 1989; U.S. Pat. No. 4,889,597 (Bourbon et. al), issued Dec. 26, 1989; and U.S. Pat. No. 4,898,647 (Moore et. al), issued Feb. 6, 1990.

A preferred embodiment of the disposable absorbent article is a diaper. As used herein, the term "diaper" refers to a garment, generally worn by infants and incontinent persons, that is worn about the lower torso of the wearer. A preferred diaper configuration for a diaper comprising an absorbent core is described generally in U.S. Pat. No. 3,860,003 (Buell), issued Jan. 14, 1975. Alternatively preferred configurations for disposable diapers herein are also disclosed in U.S. Pat. No. 4,808,178 (Aziz et. al), issued Feb. 28, 1989; U.S. Pat. No. 4,695,278 (Lawson), issued Sep. 22, 1987; U.S. Pat. No. 4,816,025 (Foreman), issued Mar. 28, 1989; and U.S. Pat. No. 5,151,092 (Buell et. al), issued Sep. 29, 1992.

Another preferred embodiment of the disposable absorbent article is a catamenial product. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987.

Preferred catamenial products can comprise wings, side flaps, and other structures and elements, as described in co-pending, commonly-assigned U.S. application Ser. No. 984,071, to Yasuko Morita, entitled "Absorbent Article Having Elasticized Side Flaps", filed Nov. 30, 1992.

It should be understood, however, that the present invention is also applicable to other absorbent articles known commercially by other names, such as incontinent briefs, adult incontinent products, training pants, diaper inserts, facial tissues, paper towels, and the like.

E. Test Methods

1. Synthetic Urine

The specific synthetic urine used in the test methods set forth herein is referred to as "Synthetic Urine". The Synthetic Urine is commonly known as Jayco SynUrine or Jayco Synthetis Urine and is available from Jayco Pharmaceuticals Company of Camp Hill, Pa. The formula for the Synthetic Urine is: 2.0 g/l of KCl; 2.0 g/l of Na2SO4; 0.85 g/l of (NH$_4$)H$_2$PO$_4$; 0.15 g/l (NH$_4$)H$_2$PO$_4$; 0.19 g/l of CaCl$_2$ and 0.23 g/l of MgCl$_2$. All of the chemicals are of reagent grade. The PH of the Synthetic Urine is in the range of 6.0 to 6.4.

2. Saline Flow Conductivity (SFC) Test

This test determines the Saline Flow Conductivity (SFC) of the gel layer formed from WAHP that is swollen in Jayco synthetic urine under a confining pressure. The objective of this test is to assess the ability of the hydrogel layer formed from a WAHP to acquire and distribute body fluids when the polymer is present at high concentrations in an absorbent member and exposed to usage mechanical pressures. Darcy's law and steady-state flow methods are used for determining saline flow conductivity. (See, for example, "Absorbency," ed. by P. K. Chatterjee, Elsevier, 1985, Pages 42–43 and "Chemical Engineering Vol. II, Third Edition, J. M. Coulson and J. F. Richardson, Pergamon Press, 1978, Pages 125–127.)

A predetermined layer of swollen absorbent material used for SFC measurements is formed by swelling an absorbent material in Jayco synthetic urine for a time period of 60 minutes. The hydrogel layer is formed and its flow conductivity measured under a mechanical confining pressure of 0.3 psi (about 2 kPa). Flow conductivity is measured using a 0.118 M NaCl solution. For a hydrogel-forming absorbent polymer whose uptake of Jayco synthetic urine versus time has substantially leveled off, this concentration of NaCl has been found to maintain the thickness of the hydrogel layer substantially constant during the measurement. For some hydrogel-forming absorbent polymers, small changes in hydrogel-layer thickness can occur as a result of polymer is swelling, polymer deswelling, and/or changes in hydrogel-layer porosity. A constant hydrostatic pressure of 4920 dyne/cm$^2$ (5 cm of 0.118 M NaCl) is used for the measurement.

Flow rate is determined by measuring the quantity of solution flowing through the hydrogel layer as a function of time. Flow rate can vary over the duration of the measurement. Reasons for flow-rate variation include changes in the thickness of the hydrogel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure.

Figure 2:
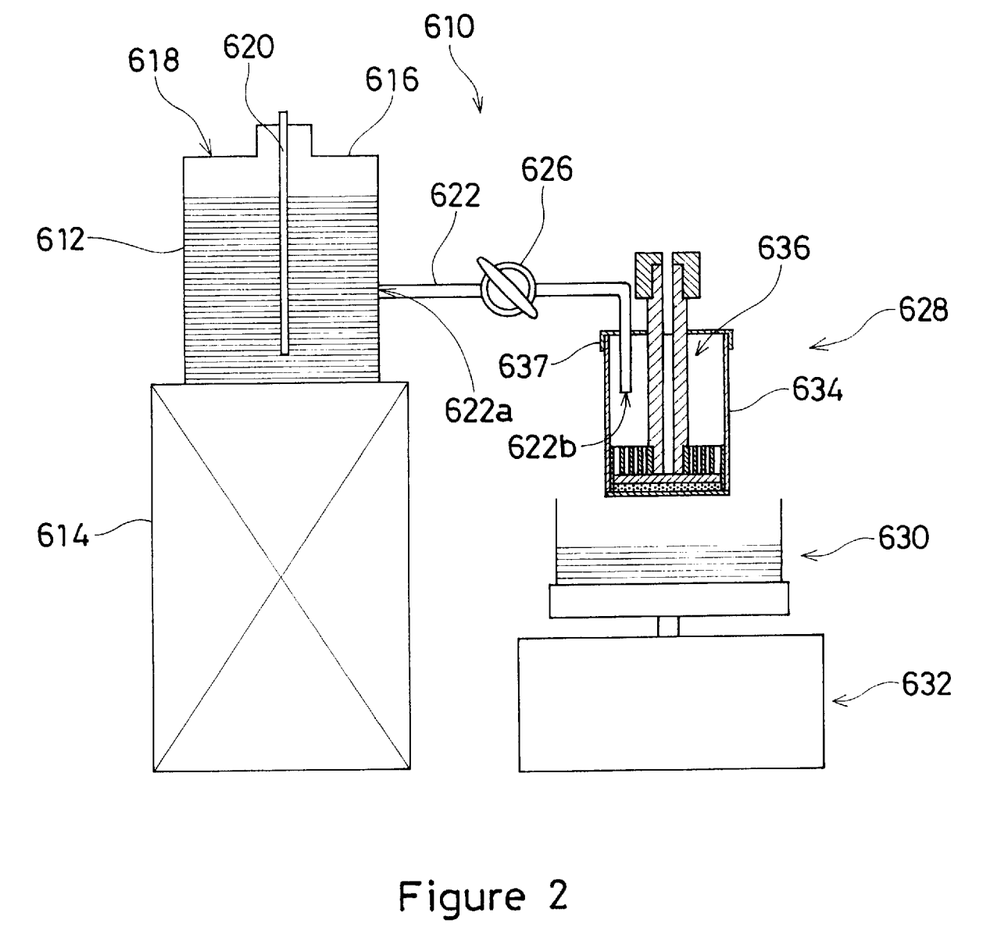
FIG. 2 is a schematic view of an apparatus for measuring the SFC value of the absorbent materials.

A suitable apparatus 610 for this test is shown in FIG. 2. This apparatus comprises a constant hydrostatic head reservoir indicated generally as 612 that sits on a laboratory jack 614. The reservoir 612 has a lid 616 with a stoppered vent 618 so that additional fluid can be added to the reservoir 612. An open-ended tube 620 is inserted through the lid 616 to allow air to enter the reservoir 612 for the purpose of delivering fluid at a constant hydrostatic pressure. The bottom end of the tube 620 is positioned so as to maintain fluid in a cylinder 634 at a height of 5.0 cm above the bottom of a WAHP layer 668 (see FIG. 3).

The reservoir 612 is provided with a generally L-shaped delivery tube 622 having an inlet 622a that is below the surface of the fluid in the reservoir. The delivery of fluid by the tube 622 is controlled by a stopcock 626. The tube 622 delivers fluid from the reservoir 612 to a piston/cylinder assembly generally indicated as 628. Beneath the assembly 628 is a support screen (not shown) and a collection reservoir 630 that sits on a laboratory balance 632.

Figure 3:
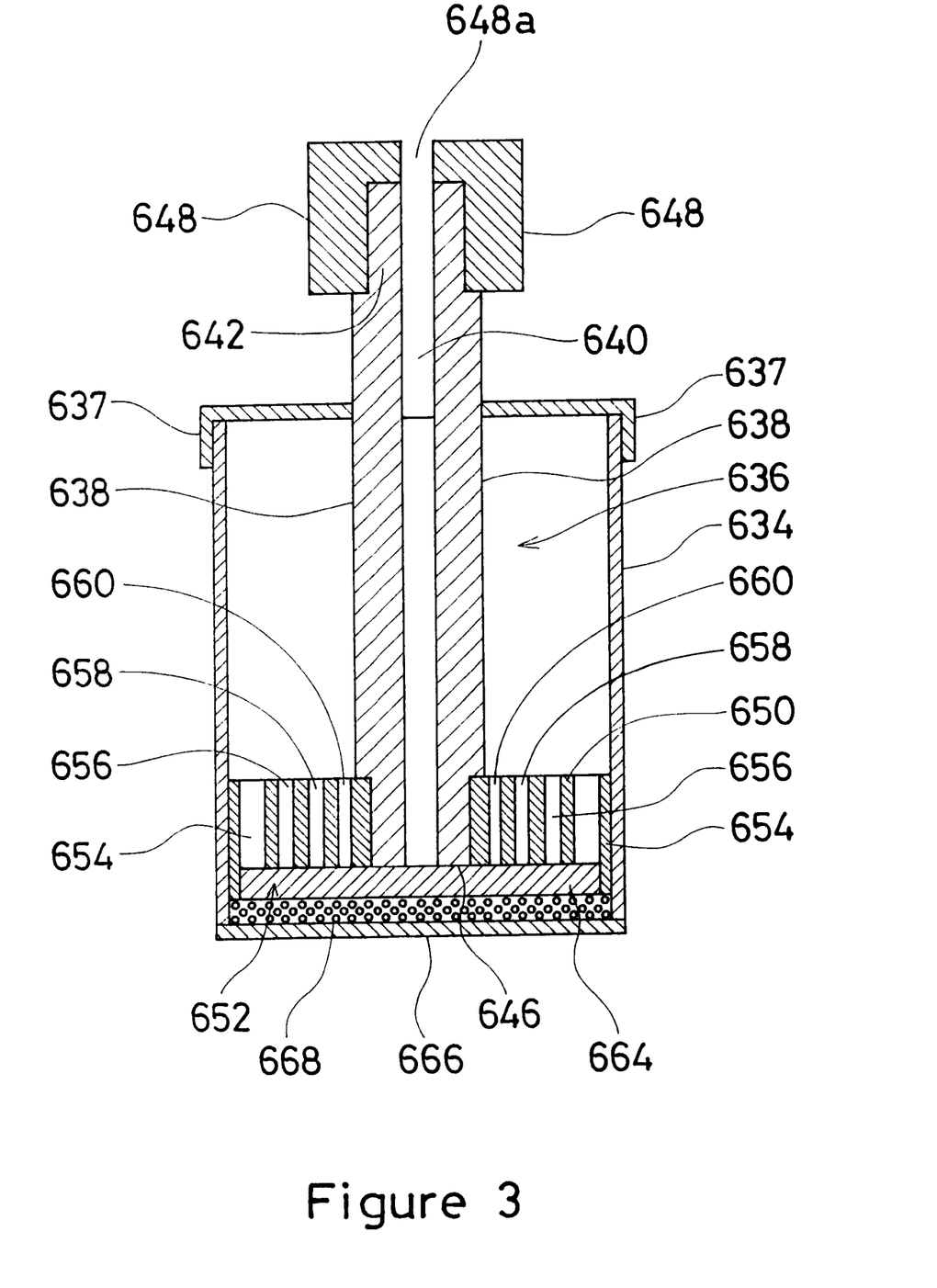
FIG. 3 represents an enlarged sectional view of the piston/cylinder assembly shown in FIG. 2.

Referring to FIG. 2, the assembly 628 basically consists of a cylinder 634, a piston generally indicated as 636 and a cover 637 provided with holes for the piston 636 and the delivery tube 622. As shown in FIG. 2, the outlet 622b of the tube 622 is positioned below the bottom end of the tube 620 and thus will also be below the surface of the fluid (not shown) in the cylinder 634. As shown in FIG. 3, the piston 636 consists of a generally cylindrical LEXAN® shaft 638 having a concentric cylindrical hole 640 bored down the longitudinal axis of the shaft. Both ends of the shaft 638 are machined to provide a first end 642 and second end 646. A weight 648 rests on the first end 642 and has a cylindrical hole 648a bored through the center thereof.

Figure 4:
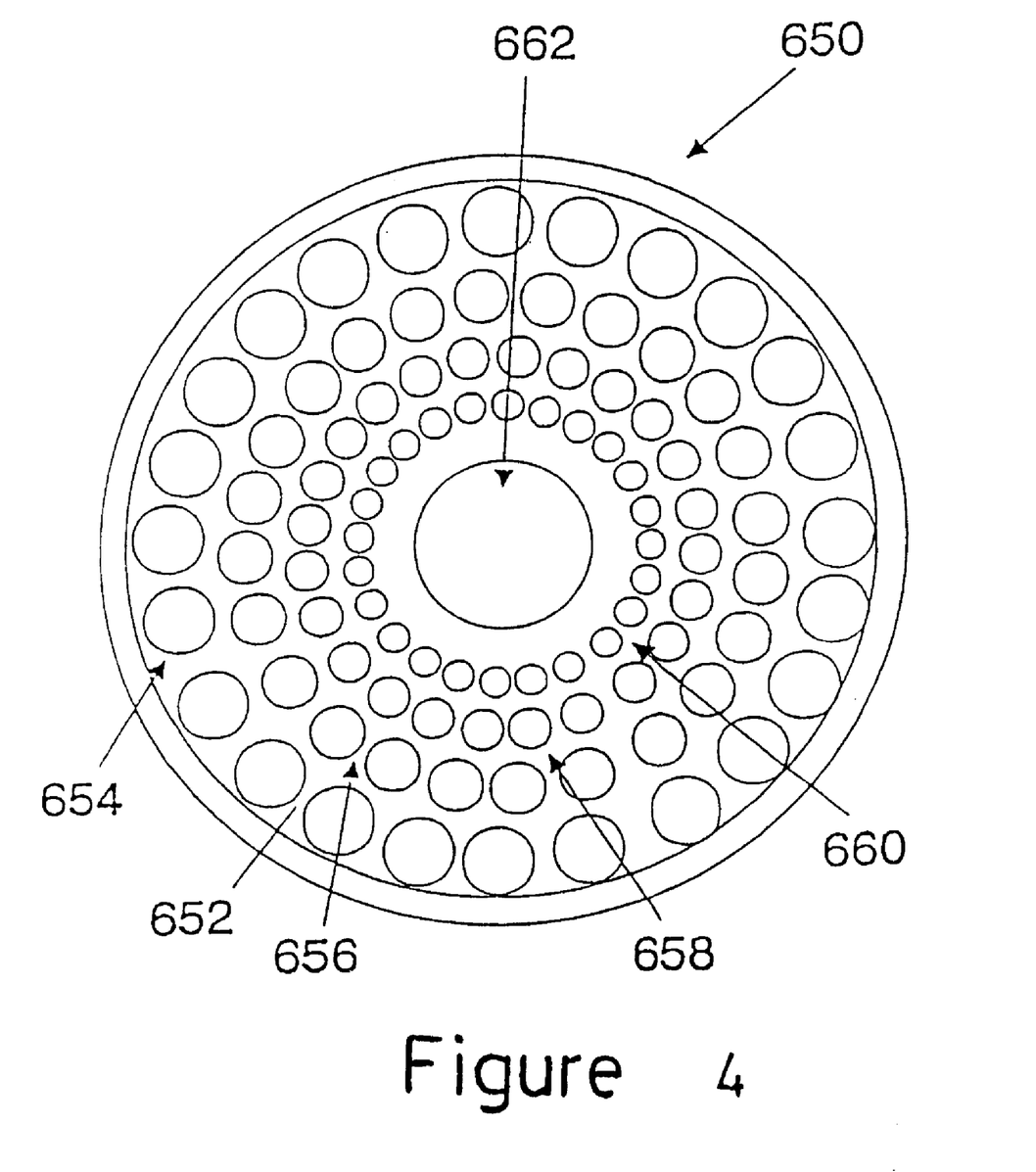
FIG. 4 represents a plan view of the bottom of the piston head from the piston/cylinder assembly shown in FIG. 3.

Inserted on the second end 646 is a generally circular Teflon piston head 650 having an annular recess 652 in the bottom thereof. The piston head 650 is sized so as to slidably move inside the cylinder 634. As particularly shown in FIG. 4, the piston head 650 is provided with four concentric rings of twenty-four cylindrical holes, each indicated generally as, a first ring 654, a second ring 656, a third ring 658, and a forth ring 660. As can be seen in FIG. 4, the concentric rings 654 to 660 fit within the area defined by a recess 652. The holes in each of these concentric rings are bored from the top to bottom of the piston head 650. The holes in each ring are spaced by approximately 15 degrees and offset by approximately 7.5 degrees from the holes in adjacent rings. The holes in each ring have a progressively smaller diameter going inwardly from the first ring 654 (0.204 inch diameter) to the forth ring 660 (0.111 inch diameter). The piston head 650 also has cylindrical hole 662 bored in the center thereof to receive, the second end 646 of the shaft 638.

As shown in FIG. 3, a fritted circular glass disc 664 fits within the recess 652. Attached to bottom end of the cylinder 634 is a No. 400 mesh stainless steel cloth screen 666 that is biaxially stretched to tautness prior to attachment. The sample of WAHP 668 is supported on the screen 666.

The cylinder 634 is bored from a transparent LEXAN® rod or equivalent and has an inner diameter of 6.00 cm (area=28.27 cm ), a wall thickness of approximately 0.5 cm, and a height of approximately 6.0 cm. The piston head 650 is machined from a solid Teflon rod. It has a height of 0.625 inches and a diameter that is slightly less than the inner diameter of the cylinder 634, so that it fits within the cylinder with minimum wall clearances, but still slides freely. The recess 652 is approximately 56 mm in diameter by 4 mm deep. The hole 662 in the center of the piston head 650 has a threaded 0.625 inch opening (18 threads/inch) for the second end 646 of the shaft 638. The fretted disc 664 is chosen for high permeability (e.g., Chemglass Cat No. CG-201-40, 60 mm diameter; X-Coarse Porosity) and is ground so that it fits snugly within the recess 652 of the piston head 650, with the bottom of the disc being flush with the bottom of the piston head. The shaft 638 is machined from a LEXAN® rod and has an outer diameter of 0.875 inches and an inner diameter of 0.250 inches. The end 646 is approximately 0.5 inches long and is threaded to match the first hole 662 in the piston head 650. The end 642 is approximately an inch long and 0.623 inches in diameter, forming an annular shoulder to support the stainless steel weight 648. Fluid passing through the hole 640 in the shaft 638 can directly access the fretted disc 664. The annular stainless steel weight 648 has an inner diameter of 0.625 inches, so that it slips onto the first end 642 of the shaft 638 and rests on the annular shoulder formed therein. The combined weight of the fretted glass disc 664, the piston 636 and the weight 648 equals 596 g, which corresponds to a pressure of 0.3 psi for an area of 28.27 cm$^2$. The cover 637 is machined from LEXAN® or its equivalent and is dimensioned to cover the top of the cylinder 634. It has an 0.877 inch opening in the center thereof for the shaft 638 of the piston 636 and a second opening near the edge thereof for the delivery tube 622.

The cylinder 634 rests on a 16 mesh rigid stainless steel support screen (not shown) or equivalent. This support screen is sufficiently permeable so as to not impede fluid flow into the collection reservoir 630. The support screen is generally used to support the cylinder 634 when the flow rate of saline solution through the assembly 628 is greater than about 0.02 g/sec. For flow rates less than about 0.02 g/sec, it is preferable that there be a continuous fluid path between the cylinder 634 and the collection reservoir.

The 0.118 M NaCl solution is prepared by dissolving 6.896 g NaCl (Baker Analyzed Reagent or equivalent) to 1.0 liters with distilled water.

An analytical balance 632 accurate to 0.01 g (e.g., Mettler PM4000 or equivalent) is typically used to measure the quantity of fluid flowing through the WAHP layer 668 when the flow rate is about 0.02 g/sec or greater. The balance is preferably interfaced to a computer for monitoring fluid quantity versus time.

The thickness of the WAHP layer 668 in the cylinder 634 is measured to an accuracy of about 0.1 mm. Any method having the requisite accuracy can be used, as long as the weights are not removed and the hydrogel layer is not additionally compressed or disturbed during the measurement. Using a caliper gauge (e.g., Manostat 15-100-500 or equivalent) to measure the vertical distance between the bottom of the stainless steel weight 648 and the top of cover 637, relative to this distance without the WAHP layer 668 in the cylinder 634 is acceptable.

The SFC measurement is performed at ambient temperature (i.e., 20°–25° C.) and is carried out as follows:

0.9 g aliquot of WAHP (corresponding to a basis weight of 0.032 g/cm$^2$) is added to the cylinder 634 and distributed evenly on screen 666. For most WAHPs, moisture content is typically less than 5%. For these, the quantity of WAHP to be added can be determined on a wet-weight (as is) basis. For WAHPs having a moisture content greater than about 5%, the added polymer weight should be corrected for moisture (i.e., the added polymer should be 0.9 g on a dry-weight basis). Care is taken to prevent WAHP from adhering to the cylinder walls. The piston 636 (minus weight 648) with the disc 664 positioned in the recess 652 of the piston head 650 is inserted into the cylinder 634 and positioned on top of the dry WAHP 668. If necessary, the piston 636 can be turned gently to more-uniformly distribute the WAHP on the screen 666. The cylinder 634 is the covered with the cover 637 and the weight 648 is then positioned on the first end 642 of the shaft 638.

A fretted disc (coarse or extra coarse) having a diameter greater than that of the cylinder 634 is positioned in a wide/shallow flat-bottomed container that is filled to the top of the fretted disc with Jayco synthetic urine. The piston/cylinder assembly 628 is then positioned on top of this fretted glass disc. Fluid from the container passes through the fretted disc and is absorbed by the WAHP 668. As the WAHP absorbs fluid, a WAHP layer is formed in the cylinder 634. After a time period of 60 minutes, the thickness of the WAHP layer is determined. Care is taken that the WAHP layer does not lose fluid or take in air during this procedure. The piston/cylinder assembly 628 is then transferred to the apparatus 610. The support screen (not shown) and any gap between it and the piston/cylinder assembly 628 is presaturated with saline solution.

The SFC measurement is initiated by adding NaCl solution through the hole 640 in the shaft 638 in order to expel air from the piston head 650 and then turning the stopcock 626 to an open position so that the delivery tube 622 delivers fluid to the cylinder 634 to a height of 5.0 cm above the bottom of the WAHP layer 668. Although the measurement is considered to have been initiated ($t_0$) at the time NaCl solution is first added, the time at which a stable hydrostatic pressure, corresponding to 5.0 cm of saline solution, and a stable flow rate is attained ($t_S$) is noted. (The time $t_S$ should typically be about one minute or less.) The quantity of fluid passing through the WAHP layer 668 versus time is determined gravimetrically for a time period of 10 minutes. After the elapsed time, the piston/cylinder assembly 628 is removed and the thickness of the WAHP layer 668 is measured. Generally the change in thickness of the hydrogel layer is less than about 10%.

In general, flow rate need not be constant. The time-dependent flow rate through the system, $F_s(t)$ is determined, in units of g/sec, by dividing the incremental weight of fluid passing through the system (in grams) by incremental time (in seconds). Only data collected for times between $t_S$ and 10 minutes is used for flow rate calculations. Flow rate results between $t_S$ and 10 minutes is used to calculate a value for $F_s$ (t=0), the initial flow rate through the WAHP layer. $F_s$ (t=0) is calculated by extrapolating the results of a least-squares fit of $F_s$ (t) versus time to t=0.

For a layer having a very high permeability (e.g., a flow rate greater than ~2 g/sec), it may not be practical to collect fluid for the full 10 minute time period. For flow rates greater than ~2 g/sec, the time of collection can be shortened in proportion to the flow rate.

For some WAHPs having extremely low permeability, absorption of fluid by the hydrogel competes with transport of fluid through the WAHP layer and either there is no flow of fluid through the WAHP layer and into the reservoir or, possibly, there is a net absorption of fluid out of the reservoir. For these extremely low permeability hydrogel layers, it is optional to extend the time for Jayco SynUrine absorption to longer periods (e.g., 16 hours).

In a separate measurement, the flow rate through the apparatus 610 and the piston/cylinder assembly 628 ($F_a$) is measured as described above, except that no WAHP layer is present. If $F_a$ is much greater than the flow rate through the system when the WAHP layer is present, $F_s$, then no correction for the flow resistance of the SFC apparatus and the piston/cylinder assembly is necessary. In this limit, $F_g = F_s$, where $F_g$ is the contribution of the WAHP layer to the flow rate of the system. However if this requirement is not satisfied, then the following correction is used to calculate the value of $F_g$ from the values of $F_s$ and $F_a$:

$$F_g = (F_a \cdot F_s)/(F_a - F_s)$$

The Saline Flow Conductivity (K) of the hydrogel layer is calculated using the following equation:

$$K = \{F_g(t=0) \cdot L_0\}/\{q \cdot A \cdot P\},$$

where $F_g(t=0)$ is the flow rate in g/sec determined from regression analysis of the flow rate results and any correction due to assembly/apparatus flow resistance, $L_0$ is the initial thickness of the WAHP layer in cm, q is the density of the NaCl solution in g/cm$^3$. A is the area of the hydrogel layer in cm$^2$. P is the hydrostatic pressure in dyne/cm$^2$, and the saline flow conductivity, K, is in units of cm$^3$ sec/g.

The average of three determinations should be reported.

3. Gel Volume

Gel volume of a WAHP is defined as its retention absorbent capacity after swollen in an excess of Jayco Synthetic Urine. It provides a measure of the maximum absorbent capacity of the polymer under conditions of use where the pressures on the polymer are relatively low. Gel volume is determined by centrifuge capacity method described below by using the Jayco Synthetic Urine. The gel volume is calculated on a dry-weight basis. The dry weight used in the gel volume calculation is determined by oven drying the WAHP at 105° C. for three hours. All of the chemicals are of reagent grade. The pH of the Jayco Synthetic Urine is in the range of 6.0 to 6.4.

Heat-sealable tea-bag paper is cut into 6 cm×12 cm, folded in half lengthwise and sealed close to the edge along two sides with a T-bar sealer to produce 6 cm×6 cm tea bag squares. 0.200(±0.005) Gram of a WAHP is transferred into a tea-bag, and the top of the bag is sealed at it's edge. The top of an empty tea-bag is sealed and is used as a blank. Approximately 300 ml of Jayco Synthetic Urine is poured into a 1,000 ml beaker, and the tea-bag containing WAHP and the blank are submerged into the beaker. After being soaked for 30 minutes, the blank and the WAHP-filled tea bag are removed from the solution by using tongs. A centrifuge (H-122 type, Kokusan Enshinki Co. Ltd., Tokyo, Japan) with a direct read tachometer, electric timer is used for this measurement. The sample tea bags and the blank tea bags are positioned in the centrifuge basket and centrifuged at 1,100 rpm for three minutes. Gel volume is calculated as follows:

$$\text{Gel volume}(g/g) = (Ws - Wb - Wo)/W_o$$

wherein Ws is the sample tea bag weight after centrifuge, Wb is the blank tea bag weight after centrifuge, $W_o$ is the WAHP weight (0.200 g).

The average of at least two determinations should be reported.

4. Extractable Component

The percentage of extractable polymer in carboxylic acid based hydrogel-forming polymers is determined by the Extractable Polymer Content Determination Carboxylic Acid Based Hydrogel-Forming Polymers method described in U.S. Reissue Pat. No. 32,649 (Brandt et. al), reissued Apr. 19, 1988, but using 0.9% saline solution, filtering the supernatant through a Whatman 0.7 micron GF/F glass microfiber filter (e.g., Catalog #1825-125) or equivalent, and calculating the extractable polymer on a dry-weight basis. It is also noted that in U.S. Reissue Pat. No. 32,649 that $V_a$ should refer to the volume of base and $V_b$ should refer to the volume of acid.

5. Percentage of Covalently Bonded Polycationic Polymer (PCBPP)

This test determines the percentage of covalently bonded polycationic polymer (PCBPP) on the surface of the gelling particles in the absorbent material. The PCBPP is determined by a colloid titration procedure, wherein absorbent material samples are stirred in an acidic water solution, and the amount of extracted polymer in the filtrate (supernatant) is titrated with 1/400 N Potassium Polyvinyl Sulfate (PVSK) standard solution by using Toluidine Blue Indicator solution as the indicator.

The particular procedure of colloid titration analysis determination for determining the PCBPP is set forth as follows:

1.0 Gram aliquot of absorbent material is weighted into a 1000 ml beaker and recorded as Ws. 500 Milliliters of 0.1 N HCl solution are added to the beaker and the mixture is stirred for 1 hour. The supernatant is separated by filtration using a filter paper. 20 Milliliters of obtained supernatant are poured into a 50 ml beaker and a few drops of Toluidine Blue Indicator solution (Wako Pure Chem. Ind., Ltd., Osaka, Japan) are added. The supernatant solution with Indicator (blue solution) is titrated with 1/400 N Potassium Polyvinyl Sulfate (PVSK) standard solution (Wako Pure Chem. Ind., Ltd., Osaka, Japan). The end point is reached when the solution turns from blue to violet.

The amount of extracted polycationc polymer We (g) from Ws gram of absorbent material sample is calculated by the following equation:

$$We = MW \cdot (Np \cdot Vp) \cdot 500/(20 \cdot 1000)$$

wherein MW is the molecular weight of the repeat unit of extracted polycationic polymer, Np is the equivalent concentration of PVSK(eq./l), Vp(ml) is the volume of PVSK needed to titrate the 20 ml supernatant from blue to violet.

The bonding percentage is calculated by the following equation:

$$PCBPP = (Wt - We)/Wt \cdot 100\%$$

wherein Wt is the total amount of polycationic polymer in Ws grams of absorbent material and is calculated by the following equation:

$$Wt = Ws \cdot Cp$$

in which Cp is the concentration of polycationic polymer in the absorbent material.

F. Precursor Particle Example

An aqueous monomer solution is prepared consisting of 4000 grams of partially neutralized acrylic acid having a 75 mol % portion thereof neutralized with caustic soda, 3.7 grams of N,N'-methylene-bis-acrylamide, and 6000 grams of water. The aqueous monomer solution is fed into the reaction vessel, which is subsequently purged with nitrogen gas to remove the remaining entrapped air from the reaction system. Then, the mixture is stirred and heated to about 45° C., and a solution of 20 grams of 2,2'-azo-bis-(2-amidinopropane)-dihydrochloride in 100 grams of water is added thereto as a polymerization initiator. Polymerization begins about 15 minutes after the addition of the polymerization initiator. With the progress of the polymerization, the aqueous monomer solution gives rise to a soft water-containing gel. The inner temperature of the reaction system is kept at 80–90° C. for several hours to further complete the polymerization. A swollen absorbent gelling polymer is formed. The resultant swollen absorbent gelling polymer thus obtained is spread on a standard #50 size metal gauge and dried with a hot air at 150° C. The dried particles are pulverized with a hammer type crusher and sifted with a standard #20 sieve (850 microns) to obtain particles that pass through the standard #20 sieve. 0.5 Parts of glycerine, 2 parts of water and 2 parts of ethyl alcohol mixture are sprayed onto 100 parts of the resulting particles. The mixture is heated at 210° C. for 10 minutes. As a result, dry white precursor absorbent gelling particles are obtained.

G. Examples

The following examples are presented for purposes of illustrating various aspects of the absorbent material of the invention and are not intended as limiting the scope of the appended claims in any way.

EXAMPLE 1

A solution is prepared consisting of 250 grams of polyallylamine solution with a concentration of 10% by weight (PAA-C, obtained from Nitto Boseki Co. Ltd., Tokyo), 1600 grams of ethanol and the balance water. The solution is applied to 2500 grams of precursor particles made in accordance with the Precursor Particle Example discussed above in a 20-liter evaporator flask. The precursor particles have a particle size such that the precursor particles pass through a standard #20 sieve (850 microns) and are retained on a standard #100 sieve (150 microns). The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resulting product is divided into 5 parts and placed into 5 trays (20 cm·25 cm). These trays are placed into an oven and heated at 200° C. for 2.5 hours. The dried absorbent material is pulverized with a hammer type crusher and sifted with a standard #20 sieve (850 microns) to obtain particles that pass through the standard #20 sieve. As a result, particulate absorbent material with light yellow color is obtained. The properties of the precursor particles made according to the Precursor Particle Example and the absorbent material made according to this Example are evaluated. The gel volume (GV) and SFC values of the precursor particles are 42 g/g and $0.8 \cdot 10^{-7}$ cm$^3$ sec/g. The gel volume (GV) and SFC values of the absorbent material are 35 g/g and $108 \cdot 10^{-7}$ cm$^3$ sec/g. Percentage of covalently bonded polyallylamine is 90%. The results surprisingly illustrate the higher liquid permeability (SFC) while maintaining a high absorbent capacity (GV).

EXAMPLE 2

Absorbent gelling particles obtained from commercial sources are used in this example. Specifically, 2500 grams of Aqualic CA L761f (lot # 4N31-021, which is obtained from Nippon Shokubai Co. Ltd., Osaka, Japan) is placed in a 20-liter rotary evaporator flask. The L761f particles are surface-crosslinked absorbent gelling particles. A solution consisting of 250 grams of polyallylamine (molecular weight 10,000) in a concentration of 10% by weight (PAA-C, obtained from Nitto Boseki Co. Ltd., Tokyo), 1600 grams of ethanol, and the balance water is poured into the flask. The mixture is thoroughly mixed with a spatula until all of the precursor particles are wetted with the above solution. The solvent in the resulting mixture is evaporated with a rotary evaporator (EYELA N-11 type, available from TOKYO RIKAKIKAI CO., LTD., Tokyo) at 60° C. The resulting product is divided into 5 parts and placed into 5 trays (20 cm·25 cm). These trays are placed into an oven and heated at 150° C. for about 16 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the commercially purchased precursor particles ("L761f") and the resulting absorbent material are evaluated and presented in Table 1 below.

TABLE 1

| Sample | Gel volume (g/g) | SFC ($10^{-7}$ cm$^3$ sec/g) | covalently bonded (%) | Extractable weight (%) |
|---|---|---|---|---|
| L761f | 37.1 | 17 | — | 11.0 |
| absorbent material | 36 | 175 | 95% | 8.2 |

The results surprisingly illustrate the higher liquid permeability (SFC) achieved by the absorbent material according to the invention and its maintained high absorbent capacity (GV) as compared to the commercially purchased L761f precursor particles which were not made according to the invention.

EXAMPLE 3

Absorbent gelling particles obtained from commercial sources are used in this example. 2500 grams of Aqualic CA L761f (lot # 4N31 obtained from Nippon Shokubai Co. Ltd., Osaka, Japan) is placed in a 20-liter rotary evaporator flask. A solution consisting of 83.3 grams of polyethylene-imine (molecular weight 70,000; Epomin P1000, obtained from Nippon Shokubai Co. Ltd., Osaka, Japan) in a concentration of 30% by weight, 1600 grams of ethanol and the balance water is poured into the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is divided into 5 parts and placed into 5 trays (20 cm·25 cm). These trays are placed into an oven and heated at 200° C. for 2.5 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the absorbent material is evaluated and presented in Table 2 below.

TABLE 2

| Sample | Gel volume (g/g) | SFC (10-7 cm3 sec/g) | covalently bonded PEI (%) | Extractable weight (%) |
|---|---|---|---|---|
| absorbent material | 35.0 | 112 | 95% | 8.9 |

Again, the absorbent material according to the invention possesses high liquid permeability (SFC) and maintains high absorbent capacity (GV).

EXAMPLE 4

Absorbent gelling particles obtained from commercial sources are used in this example. 2500 grams of Aqualic CA L761f (lot # 4N31 obtained from Nippon Shokubai Co. Ltd., Osaka, Japan) is placed in a 20-liter rotary evaporator flask. A solution consisting of 83.3 grams of polyethylene-imine (molecular weight 70,000; Epomin P1000, obtained from Nippon Shokubai Co. Ltd., Osaka, Japan) in a concentration of 30% by weight, 1600 grams of ethanol and the balance water is poured into the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is divided into 5 parts and placed into 5 trays (20 cm·25 cm). These trays are placed into an oven and heated at 150° C. for 6 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the absorbent material is evaluated and presented in Table 3 below.

EXAMPLE 5

Absorbent gelling particles obtained from commercial sources are used in this example. 2500 grams of Aqualic CA L761f (lot # 4N31 obtained from Nippon Shokubai Co. Ltd., Osaka, Japan) is placed in a 20-liter rotary evaporator flask. A solution consisting of 250 grams of polyallylamine (molecular weight 10,000) in a concentration of 10% by weight, 1600 grams of ethanol and the balance water is poured into the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is divided into 5 parts and placed into 5 trays (20 cm·25 cm). These trays are placed into an oven and heated at 180° C. for 2 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the absorbent material is evaluated and presented in Table 3 below.

EXAMPLE 6

Absorbent gelling particles obtained from commercial sources are used in this example. 250 grams of Aqualic CA L761f (lot # 4N31 obtained from Nippon Shokubai Co. Ltd., Osaka, Japan) is placed in a 20-liter rotary evaporator flask. A solution consisting of 25 grams of polyallylamine (molecular weight 10,000) in a concentration of 10% by weight, 160 grams of ethanol and the balance water is poured into the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is divided into 10 parts and placed into 10 trays (10 cm×13 cm). These trays are placed into an oven and heated at 200° C. for 0.5 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the absorbent material is evaluated and presented in Table 3 below.

EXAMPLE 7

Absorbent gelling particles obtained from commercial sources are used in this example. 250 grams of Aqualic CA L761f (lot # 4N31 obtained from Nippon Shokubai Co. Ltd., Osaka, Japan) is placed in a 20-liter rotary evaporator flask. A solution consisting of 8.33 grams of polyethylene-imine (molecular weight 70,000; Epomin P1000, obtained from Nippon Shokubai Co. Ltd., Osaka, Japan) in a concentration of 30% by weight, 160 grams of ethanol and the balance water is poured into the flask. The mixture is thoroughly mixed with a spatula until all of the precursor particles are wetted with the above solution. The solvent included in the resultant mixture is evaporated with a rotary evaporator (EYELA N-11 type, available from TOKYO RIKAKIKAI CO., LTD., Tokyo) at 60° C. The resultant product is divided into 10 parts and placed into 10 trays (10 cm·13 cm). These trays are placed into an oven and heated at 200° C. for 0.5 hours. The heated absorbent material is pulverized with a hammer type crusher and sifted with a standard #20 sieve (850 microns) to obtain particles that pass through the standard #20 sieve. As a result, particulate absorbent material with light yellow color is obtained. The properties of the absorbent material is evaluated and presented in Table 3 below.

TABLE 3

| Sample | Gel volume (g/g) | SFC ($10^{-7}$ cm3 sec/g) |
|---|---|---|
| example 4 | 37.0 | 103 |
| example 5 | 34.0 | 121 |

TABLE 3-continued

| Sample | Gel volume (g/g) | SFC ($10^{-7}$ cm3 sec/g) |
|---|---|---|
| example 6 | 35.0 | 121 |
| example 7 | 35.0 | 119 |

The absorbent material of example 4 through 7 according to the present invention possesses high liquid permeability (SFC) and maintains high absorbent capacity (GV).

COMPARATIVE EXAMPLES

The properties of the commercially available absorbent gelling particles are evaluated and presented in Table 4 below.

TABLE 4

| Sample | maker | Gel volume (g/g) | SFC ($10^{-7}$ cm3 sec/g) |
|---|---|---|---|
| SXM100 | Stockhousen | 43.0 | 3 |
| XP30 | Nalco | 35.0 | 57 |
| XP20 | Nalco | 35.0 | 43 |
| L76lf | NSKK | 38.0 | 18 |
| L74 | NSKK | 42.0 | 0.2 |

Stockhausen: Stockhausen GmbH, Germany
Nalco: Nalco Chemical Co., Illinois, US
NSKK: Nippon Shokubai Co., Ltd., Osaka, Japan All publications, patent applications, and issued patents mentioned orherein above are hereby incorporated in their entirety by reference.

It is understood that the examples and embodiments described herein are for illustrative purposes only and that various modifications changes in light thereof will be suggested to one skilled in the art and to be included in the sprit and purview of this application and scope of the appended claims.

What is claimed is:

1. An absorbent material comprising the reaction product of:
   (a) a water-insoluble, absorbent, hydrogel-forming polymer; and
   (b) a polycationic polymer;
   wherein the reaction forms covalent bonds between the water-insoluble, absorbent, hydrogel-forming polymer and the polycationic polymer, the absorbent material is in particulate form and has a Saline Flow Conductivity greater than $(500-11.5 \cdot GV)(10^{-7})$ cm$^3$ sec/g, wherein GV is the gel volume of the absorbent material.

2. The absorbent material of claim 1 wherein the absorbent material has a Saline Flow Conductivity of at least about $20 \cdot (10^{-7})$ cm$^3$ sec/g.

3. The absorbent material of claim 2 wherein the absorbent material has a Saline Flow Conductivity greater than $(500-11.0 \cdot GV)(10^{-7})$ cm$^3$ sec/g.

4. The absorbent material of claim 1 wherein at least about 80% by weight of the polycationic polymer is covalently bonded to the absorbent gelling particles.

5. The absorbent material of claim 4 wherein at least about 90% by weight of the polycationic polymer is covalently bonded to the absorbent gelling particles.

6. The absorbent material of claim 1 wherein the absorbent gelling particles have a median particle size in the range of from about 100 to about 800.

7. The absorbent material of claim 1 wherein the polycationic polymer is selected from the group consisting of polyamines, polyimines and mixtures thereof.

8. The absorbent material of claim 7 wherein the polyamides are selected from the group consisting of a polyvinylamine, a polyallylamine, and mixtures thereof.

9. The absorbent material of claim 7 wherein the polyimines are selected from the group consisting of polyethyleneimine, modified polyethyleneimines crosslinked with epihalohydrine and mixtures thereof.

10. An absorbent article comprising:

(a) a liquid pervious topsheet;

(b) a liquid impervious backsheet; and (c) an absorbent core positioned between the topsheet and the backsheet, wherein the absorbent core includes an absorbent material comprising the reaction product of:

(i) a water-insoluble, absorbent, hydrogel-forming polymer; and (ii) a polycationic polymer;

wherein the reaction forms covalent bonds between the water-insoluble, absorbent, hydrogel-forming polymer and the polycationic polymer, the absorbent material is in particulate form and has a Saline Flow Conductivity greater than $(500-11.5 \cdot GV)(10^{-7})$ cm$^3$ sec/g, wherein GV is the gel volume of the absorbent material.

11. A method of making an absorbent material comprising:

(a) preparing a solution containing a polycationic polymer and a solvent;

(b) applying the solution to a plurality of absorbent gelling particles comprising a water-insoluble, absorbent, hydrogel-forming polymer; and (c) reacting the polycationic polymer with the absorbent gelling particles so as to form covalent bonds therebetween such that the resulting absorbent material has a Saline Flow Conductivity greater than $(500-11.5 \cdot GV)(10^{-7})$ cm$^3$ sec/g, wherein GV is the gel volume of the absorbent material.

12. The method of claim 11 wherein step (c) further comprises heating the resulting material of step (b) at a temperature of from about 100° C. to about 350° C.

13. The method of claim 12 wherein the heating temperature is from about 150° C. to about 250° C.

14. The method of claim 11 further comprising removing the solvent from the resulting material of step (c).

15. The method of claim 14 wherein the step of removing the solvent comprises evaporating the solvent from the resulting material of step (c).

16. The method of claim 11 wherein the solution contains from about 0.05% to about 60% by weight of the polycationic polymer.

17. The method of claim 11 wherein the polycationic polymer is selected from the group consisting of polyamines, polyimines and mixtures thereof.

18. The method of claim 17 wherein the polyamines are selected from the group consisting of a polyvinylamine, a polyallylamine, and mixtures thereof.

19. The method of claim 17 wherein the polyimines are selected from the group consisting of polyethyleneimine, modified polyethyleneimines crosslinked with epihalohydrine and mixtures thereof.

20. An absorbent material made according to the method recited in claim 11.

21. A method for making an absorbent material comprising:

(a) preparing a solution containing a polycationic polymer and a solvent;

(b) applying the solution onto a plurality of absorbent gelling particles comprising a water-insoluble, absorbent, hydrogel-forming polymer;

(c) reacting a polycationic polymer with the absorbent gelling particles;

(d) removing the solvent from the resulting material of step (c); and (e) heating the resulting material of step (d) at a temperature of from about 100° C. to about 350° C. such that to achieve at least about 80% by weight of polycationic polymer become covalently bonded to the absorbent gelling particles.

* * * * *

UNITED STATES PATENT AND TRADEMARK OFFICE
CERTIFICATE OF CORRECTION

PATENT NO.     : 6,011,196
DATED          : January 4, 2000
INVENTOR(S)    : Wang et al.

It is certified that error appears in the above-identified patent and that said Letters Patent is hereby corrected as shown below:

<u>Title page,</u>
Item [30], Foreign Application Priority Data, please delete "PN 5371" and insert therefor -- PN 5731 --.

<u>Column 5,</u>
Line 59, please delete "SFC = (500 - 11.5 • GV) - ($10^{-7}$) cm$^3$" and insert therefor -- SFC = (500 - 11.5 • GV) • ($10^{-7}$) cm$^3$ --.

<u>Column 7,</u>
Line 25, please delete "crosslin king" and insert therefor -- crosslinking --.

<u>Column 11,</u>
Line 12, please delete "150 g/m$^2$" and insert therefor -- 150 g/m$^2$ --.

<u>Column 12,</u>
Line 24, please delete "et. al)" and insert therefor -- et al. --.

<u>Column 13,</u>
Line 16, after "polymer" please delete "is".

<u>Column 14,</u>
Line 23, please delete "(area=28.27 cm )" and insert therefor -- (area=28.27 cm$^2$) --.

<u>Column 17,</u>
Line 23, please delete "Determination Carboxylic" and insert therefor -- Determination-Carboxylic --.

UNITED STATES PATENT AND TRADEMARK OFFICE
CERTIFICATE OF CORRECTION

PATENT NO. : 6,011,196
DATED : January 4, 2000
INVENTOR(S) : Wang et al.

It is certified that error appears in the above-identified patent and that said Letters Patent is hereby corrected as shown below:

<u>Column 23,</u>
Lines 1-2, please delete "polya-mides" and insert therefor -- polyamines --.

Signed and Sealed this

Thirteenth Day of July, 2004

JON W. DUDAS
*Acting Director of the United States Patent and Trademark Office*